(12) United States Patent
Konzak

(10) Patent No.: US 6,696,294 B1
(45) Date of Patent: Feb. 24, 2004

(54) METHODS FOR GENERATING AND IDENTIFYING MUTANT POLYPLOID PLANTS, AND USES THEREFOR

(75) Inventor: Calvin F. Konzak, Pullman, WA (US)

(73) Assignee: Northwest Plant Breeding Co., Pullman, WA (US)

( * ) Notice: Subject to any disclaimer, the term of this patent is extended or adjusted under 35 U.S.C. 154(b) by 0 days.

(21) Appl. No.: 09/719,880

(22) PCT Filed: Jun. 18, 1999

(86) PCT No.: PCT/US99/13801
§ 371 (c)(1),
(2), (4) Date: Dec. 18, 2000

(87) PCT Pub. No.: WO99/65292
PCT Pub. Date: Dec. 23, 1999

Related U.S. Application Data
(60) Provisional application No. 60/089,822, filed on Jun. 19, 1998.

(51) Int. Cl.$^7$ .............................. A01H 1/06; A01H 1/00; A01H 1/02; C12N 15/01; C12N 15/00
(52) U.S. Cl. ...................... 435/441; 435/444; 435/440; 435/447; 435/446; 435/445; 435/443; 800/276; 800/270; 800/260
(58) Field of Search ............................... 800/276, 270, 800/260, 295, 298, 320, 320.3; 435/410, 444, 447, 446, 441, 440

(56) References Cited

U.S. PATENT DOCUMENTS
5,124,504 A   6/1992   Gresshoff et al.
6,143,963 A   11/2000  Keeling et al.

FOREIGN PATENT DOCUMENTS
WO   WO 98/15621 A1   4/1998

OTHER PUBLICATIONS

Sharma et al., Cereal Research Communication, vol. 17, No. 1, 1989, pp 31–34.*

Konzak, C.F., "Role of Induced Mutations." In. Crop Breeding A Cont. Basis, Vose & Blixt(eds), Pergamon Press, Oxford & New York 1984.*

Oda et al. A bread wheat mutant with low amylose content induced by Ethylmethanesulphonate. Japan J. Breed. 1992, vol. 42, pp. 151–154.*

Yamamori et al. Production of waxy wheat by genetically eliminating WX proteins. Institute of radiation breeding gamma field symposia. 1994, No 33, pp. 63–72.*

Shakoor, A., et al., "Selection for Useful Semi–Dwarf Mutants Through Induced Mutation in Bread Wheat," Proc. 5$^{th}$ Int'l Wheat Genet. Symp., pp. 540–546 (1979).

Xiaochun, Z. and P.J. Sharp, "Wheat 'Waxy' Proteins: SDS–PAGE Separation and Variation in Australian Cultivars," Proc. Wheat Breeding Soc. of Australia, pp. 253–256 (1994).

Nakamura, T., et al., "Decrease of Waxy (Wx) Protein in Two Common Wheat Cultivars With Low Amylose Content," Plant Breeding, 111:99–105 (1993).

Nakamura, T., et al., "Expression of HMW Wx Protein in Japanese Common Wheat (Triticum aestivum L.) Cultivars," Japan J. Breed., 42:681–685 (1992).

Kar, G.N., et al., "Induction of Useful Mutations in Bread Wheat," Proc. 5$^{th}$ Int'l Wheat Genet. Symp., pp. 503–509 (1979).

Siddiqui, K.A., et al., "Induced Variability for Useful Agronomic Traits in Bread Wheat," Proc. 5$^{th}$ Int'l Wheat Genet. Symp., pp. 547–558 (1979).

Yasui, T., et al., "Waxy Endosperm Mutants of Bread Wheat (Triticum aestivum L.) and Their Starch Properties," Breeding Sci., 47:161–163 (1997).

Kiribuchi–Otobe, C., et al., "Allelism Test of Waxy Hexaploid Wheats from Different Sources," Breeding Sci., 48:93–94 (1998).

Kiribuchi–Otobe, C., et al., "Production of Hexaploid Wheats with Waxy Endosperm Character," Cereal Chem., 74(1):72–74 (1997).

Nakamura, T., et al., "Production of Waxy (Amylose–Free) Wheats," Mol. Gen. Genet., 248:253–259 (1995).

Yasui, T., et al., "Amylose and Lipid Contents, Amylopectin Structure, and Gelatinisation Properties of Waxy Wheat (Triticum aestivum) Starch," J. Cereal Sci., 24:131–137 (1996).

Clark, J.R., et al., "Nucleotide Sequence of a Wheat (Triticum aestivum L.) cDNA Clone Encoding the Waxy Protein," Plant Mol. Biol., 16:1099–1101 (1991).

(List continued on next page.)

Primary Examiner—Anne Marie Grunberg
(74) Attorney, Agent, or Firm—Christensen O'Connor Johnson Kindness PLLC

(57) ABSTRACT

The present invention provides methods for generating and identifying mutations in any target gene of a polyploid plant species. In a preferred aspect of the present invention, a plant is constructed and/or selected that has at least one copy of a functional, target gene located exclusively in only one of its homoeologous, or homologous, genomes. Seed derived from the selected plant are then contacted with an effective amount of at least one mutagenic agent, the treated seed are germinated and the seeds or plants derived therefrom, are screened for mutations in the target gene. Thus, the inventive concepts set forth herein can be used to create, select and identify mutations in any target gene of any suitable polyploid plant, thereby providing a source of numerous, readily-identifiable mutations that can, if so desired, be used in crosses to develop unique new crop cultivars. New alleles of homologous or homoeologous target genes can be recombined to generate an almost unlimited range of genetically-controlled novel phenotypes having predetermined, desirable properties.

18 Claims, 3 Drawing Sheets

OTHER PUBLICATIONS

Yamamori, M., et al., "Variations in the Content of Starch-Granule Bound Protein Among Several Japanese Cultivars of Common Wheat (*Triticum aestivum* L.)," *Euphytica*, 64:215–219 (1992).

Nakamura, T., et al., "Identification of Three Wx Proteins in Wheat (*Triticum aestivum* L.)," *Biochem. Genet.*, 31(1/2):75–86 (1993).

Oda, S., et al., "A Bread Wheat Mutant with Low Amylose Content Induced by Ethyl Methanesulphonate," *Japan J. Breed.*, 42:151–154 (1992).

Yamamori, M. and T. Nakamura, "Production of a Waxy Wheat by Genetically Eliminating Wx Proteins," Gamma Field Symposium, No. 33 (1994).

Little, R., "An Attempt to Induce Resistance to *Septoria nodorum* and *Puccinia graminis* in Wheat Using Gamma Rays, Neutrons and EMS as Mutagenic Agents," *Proc. Mutation Breeding for Disease Resistance*, IAEA–PL–412–15, pp. 139–149 (1971).

Sharma, D.L., et al., "Induced Mutations for Leaf Rust Resistance," *Cereal Res. Comm.*, 17(1):31–34 (1989).

Manual on Mutation Breeding–Tech. Reports Series 119, IAEA, Vienna (1977).

Konzak, C.F., "Role of Induced Mutations." In. Crop Breeding–A Contemporary Basis, P.B. Vose and S.G. Blixt (eds)., Pergamon Press, Oxford and New York. 1984.

Micke, A. et al., *Tropic Agric.* (*Trinidad*), 64:259–277 (1987).

Nakamura et al., *Japanese Journal of Breeding*, 42:681–685 (1992).

Yamamori et al., *Euphytica*, 64:215–219 (1992).

Chao et al., *Theor. Appl. Genet.*, 78:495–504.

* cited by examiner

METHODS FOR GENERATING AND IDENTIFYING MUTANT POLYPLOID PLANTS, AND USES THEREFOR

CROSS-REFERENCE TO RELATED APPLICATION

This application claims the benefit of U.S. Provisional Application No. 60/089,822, filed Jun. 19, 1998.

FIELD OF THE INVENTION

This invention relates to genetic mutations and in particular to methods of generating and identifying genetic mutations in polyploid plant species.

BACKGROUND OF THE INVENTION

In eukaryotic organisms, genetic information is encoded by DNA strands organized into sets of several chromosomes, or genomes, located within the cell nucleus. An organism containing a single copy of each chromosome set is referred to as a genetically monoploid organism. A convenient abbreviation for the monoploid complement of chromosomes is the letter "n". For example, wheats have a basic monoploid complement of seven chromosomes, thus n=7. Most eukaryotic organisms, however, contain two copies of each member of the monoploid complement of chromosomes and are referred to as being genetically diploid (2n), with each chromosome existing as a member of a homologous pair of chromosomes. In some organisms, the diploid genome (i.e., the sum total of the genetic information encoded by the diploid number of chromosomes) is further duplicated to yield a chromosome complement consisting of multiple copies of the monoploid set of chromosomes.

Polyploid, is the generic term for an organism having more than the diploid number of chromosome sets, or genomes. Polyploidy is predominantly, although not exclusively, found in plants, especially within the agriculturally important cereal species, such as wheat and oats. Over the course of agricultural history, numerous polyploid varieties of crop species have evolved, possibly because of the improved vigor, larger grain or plant size often associated with polyploidy. Polyploidy may naturally arise by the spontaneous duplication of one or more genomes (autopolyploidy), or by the much more common process of genetically combining two or more genomes, or complete sets of chromosomes, from genetically different parents (allopolyploidy). For example, the spontaneous, natural doubling of the chromosome set of a diploid (2n) species, results in the creation of a novel autotetraploid (4n) species. The two diploid (2n) genomes that constitute the autotetraploid (4n) genome are referred to as homologous genomes, because they are genetically identical, having arisen by the duplication of a single diploid genome.

However, the true nature of autotetraploids is more complicated than appears, because true autoploids, whether spontaneous or artificially induced, are rarely fully fertile or genetically stable. All apparent autotetraploid species are only reproducible because their genomes have to some degree diverged, even though some pairs of genes show tetrasomic inheritance. A cross between two genetically divergent diploid (2n) species, in which reduction division during meiosis fails to occur, results in an allotetraploid (4n) species. In the case of the allotetraploid, however, the two diploid (2n) genomes that constitute the allotetraploid (4n) genome, are referred to as homoeologous genomes, because although they are genetically very similar, they are not genetically identical, having arisen by the fusion of two, comparatively different, independently evolved, diploid genomes.

The genetic information on the DNA strands of the chromosomes of all organisms is located in discrete segments of the chromosome DNA, termed genes. All genetic differences among natural (or artificial) species and varieties, results from mutational modifications in the structure and function of the genes. Such structural gene modifications in natural species and varieties are considered to have occurred spontaneously. The probable basis for such modifications is unknown, but there is evidence indicating that errors in DNA synthesis do infrequently occur, perhaps initiated by a wide variety of environmental and nutritional conditions. Mutations are important, in that they form the entire genetic basis for the evolution of species in nature and the basis for the artificial development of new plant cultivars. If enough different mutational variations are accumulated, the mutations form the basis for the development of new sub-species and species variations in all organisms, not only in plants.

In more modern times, geneticists and plant breeders have used mutation induction technology to supplement or complement the naturally-occurring genetic variations to improve numerous characteristics or properties of plants. Mutagen treatment technology has evolved over a long period of years, and only in the past 10 years or so has mutation induction, as a method to improve plants, become a technology of increasing acceptance. Although some methods for mutagen application have been described in the literature, and are useful, new techniques have been developed more recently that are significantly more effective and efficient in terms of resources. The mutagenesis technology embodied in this invention, represents an advance from the methods described in available literature (IAEA Manual on Mutation Breeding-Tech. Reports Series 119, IAEA, Vienna, 1977). Mutagenesis technologies in use for plant genetics and breeding research today, especially for small grain cereals mostly involve applications of the mutagens to seeds. The most widely used mutagens include electromagnetic radiations, X-rays and gamma rays, and nuclear radiations, such as thermal or fast neutrons, mainly because the sources of these radiations are more available. More commonly, chemical mutagens are now used in research; the preferred chemical agents are such alkylating agents as ethyl methanesulfonate (EMS), and diethyl sulfate (DES). In addition, azide in the form of sodium or potassium azide is now widely used. Less commonly employed for mutation induction are the more hazardous carcinogenic agents, such as N-methyl nitrosourea and N-ethyl nitrosourea, and the highly carcinogenic nitrogen mustard, 2-chloroethyl-dimethylamine. The nitrosoureas are especially active mutagens (*Maluszinski, M*. Acta. Soc. Bot. Pol. 51:429–440, 1982) whereas use of the nitrogen mustards poses a significant health risk to the user because these compounds are highly toxic to humans. More recently, as cell (microspore) and tissue culture research have evolved, attention is being given to the application of mutagens to accelerate the frequency of mutations regenerable from such cultures. However, mutagenesis technology in cultures is still in its developmental infancy, as are applications of the technology for plant improvement.

Most applications of mutagens to produce useful variants in crop plant species have had a primary goal, such as reducing plant height, reducing grain shattering, or changing the photoperiod response, traits for which the genetic basis in the mutagenized variety was previously unknown. Even so, unexpected, as well as expected results have been achieved from many studies. As a result, many new cultivars of crop plants have been developed via the direct release of a genetic line differing from the original genotype by an induced mutation (Konzak, C. F., Role of Induced Mutations, 1983, pp. 216–292. In: Crop Breeding-a Contemporary Basis. P. B. Vose and S. G. Blixt (eds). Pergamon Press, Oxford and New York; Micke, A. and Donini, B., 1987, Tropic. Agric. (Trinidad) 64:259–277). An even larger number of new cultivars of crop plants have been developed using induced mutations as new genetic variability, demonstrating that induced mutations not only can be useful, but also that they can be used in breeding to advance the potential yield, quality or disease resistance, of many crops (Micke, A. and Donini, B., 1987, Tropic. Agric. (Trinidad) 64:259–277). However, there remains a need for a method of inducing a wide range of mutations that is generally applicable to crop plants. Typically, mutagens have been applied to seeds of various species to induce mutations that might be expected to occur, based on an expectation that such genetic variation should be inducible. In most of the examples described in the literature, the actual numbers of mutations of a general phenotype generally have been sufficiently high for other scientists to recognize them as being induced, especially the relatively common mutations of semi-dwarf, or reduced height phenotypes. But, even among these more frequent types of mutations, those at the same gene locus have been rarely isolated in the same experiment. Thus, the primary evidence that the new phenotypic/genotypic variants are induced mutations, has largely been assumed because of the simultaneous recovery of many other mutant phenotypes in the same study. Studies to induce white seed coat color in wheat, for example, have been successfully carried out in red seed coat wheats, without knowledge of the genetic structure of the mutagenized wheat genotype for genes controlling the seed coat color, though seed coat color in wheat is known to be controlled by three homoeologous gene pairs, located in the A, B and D genomes. In recent, unpublished work, Warner isolated 3 white-seeded 'mutants' in Chinese Spring wheat, a genotype widely known to carry only 1 dominant red seed coat color gene. The three "mutants" were essentially identical, hence may have originated from a single event, for which the frequency is sufficiently low that a spontaneous origin cannot be ruled out.

There is a continuing need to identify new mutants, having novel, desirable characteristics, within agriculturally important plant species. Novel mutations might convey for example, increased resistance to drought or cold, reduced plant height, non-shattering of grain, resistance to preharvest sprouting, as well as new, or modified quality characteristics, offering new market use opportunities, or might result in higher crop yields. Further, it is desirable to generate numerous mutations within a plant species in order to obtain novel phenotypes, which can be intercrossed to develop novel plant cultivars having defined, more desirable characteristics of economic value. The process of identifying novel mutations within polyploid species is complicated, however, by the fact that most mutations are recessive, i.e., the mutant phenotype is not apparent in the presence of one or more copies of the non-mutated, dominant gene. Thus, the phenotype of most mutants will not be apparent in a polyploid species unless all copies of the relevant gene bear the same mutation. Since polyploids, as the term is used herein, generally contain two or more pairs of each gene, the probability of fortuitously generating an individual plant having all copies of a gene mutated in a similar manner is very slight. Thus, there is a need for a method that is generally applicable to polyploid plant species, which permits the creation and selection of a large number of mutations in any desired, target gene.

SUMMARY OF THE INVENTION

The present invention provides methods for generating and identifying mutations in any target gene of a polyploid plant species. In one aspect of the present invention, a plant is selected that has at least one pair of functional, target genes located exclusively in only one of its homoeologous, or homologous, genomes. Seed derived from the selected plant are then contacted with an effective amount of at least one mutagenic agent, the treated seed are germinated and the seeds or plants derived therefrom, are screened for mutations in the target gene. In a presently preferred embodiment of the present invention, the selected plant is a cereal crop plant and the mutagenic agent is a sequentially applied combination of ethyl methane sulfonate followed by sodium azide. In another aspect of the present invention, selective matings are made to construct plant genotypes with a functional target gene pair exclusively in only one of their homoeologous, or homologous, genomes. Seed derived from the constructed plants are then contacted with an effective amount of at least one mutagenic agent, the treated seed are germinated and the seed or plants derived therefrom, are screened for mutations in the target gene. In a presently preferred embodiment of this aspect of the present invention, the constructed plant is a cereal crop plant and the mutagenic agent is a sequentially-applied combination of ethyl methane sulfonate followed by sodium azide. In yet another aspect of the present invention, polyploid wheat plants, mutated in accordance with the methods of the present invention, are provided that include mutations in all copies of the waxy gene and so synthesize starch that has a reduced amount of, or completely lacks, amylose. Thus, the inventive concepts set forth herein can be used to create, select and identify mutations in any target gene of any suitable polyploid plant. The mutations generated in accordance with the present invention provide a source of numerous, readily-identifiable mutations that can, if so desired, be used as germplasm to generate novel new plant cultivars, or the novel induced mutant alleles in different genomes of the polyploid, can intercrossed to generate novel phenotypes having predetermined, desirable properties.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
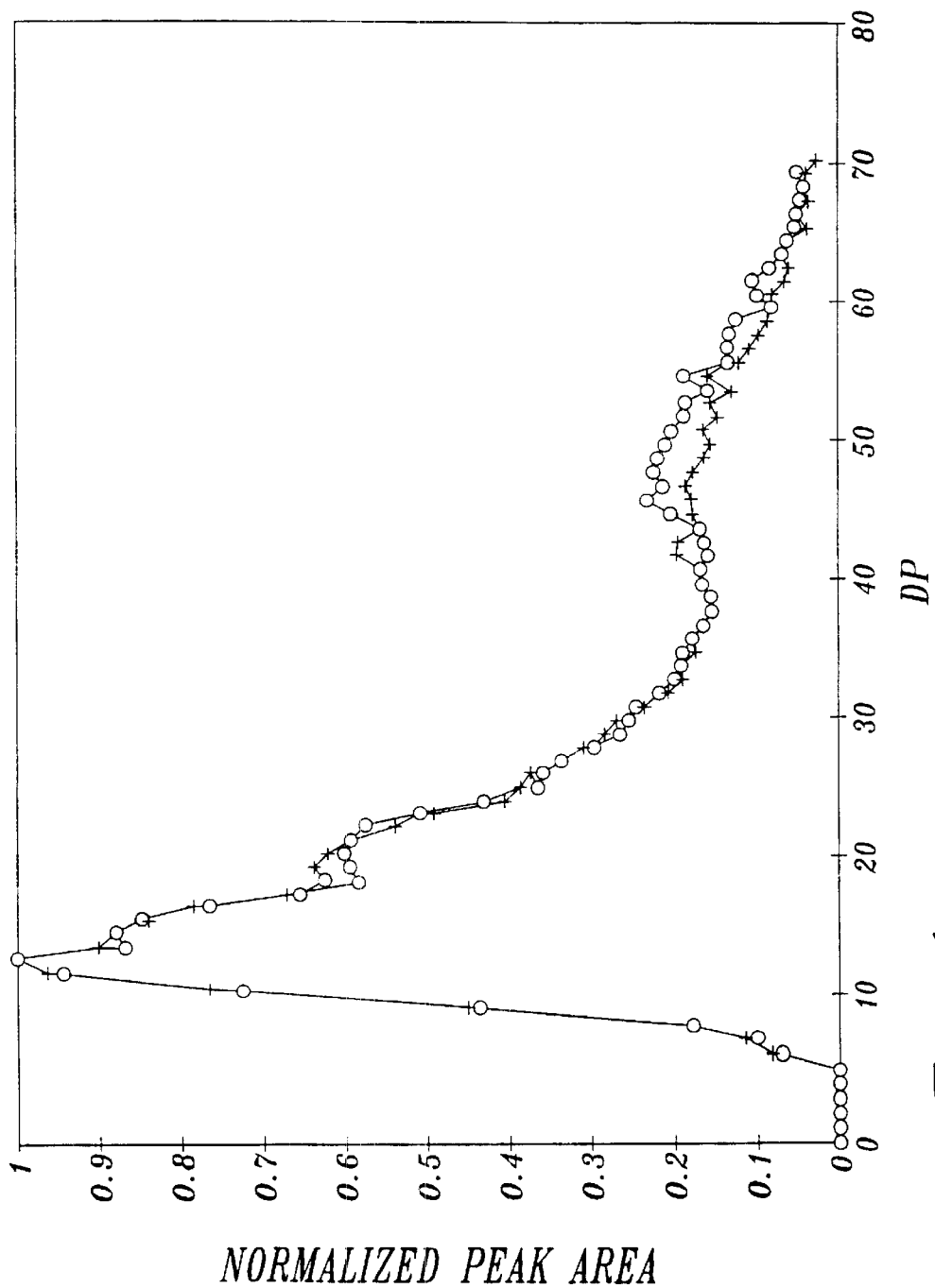
FIG. 1 graphically illustrates the distribution of polymer size of starch molecules derived from way wheat mutant 18 (closed diamonds) and from waxy wheat mutant 21 (open circles). The x-axis represents the normalized peak area that is indicative of the amount of starch molecules having a degree of polymerization that is indicated by the y-axis.

The inventive concepts set forth herein can be used to create, select, and identify mutations in any target gene of any suitable polyploid plant, thereby providing a source of numerous, readily-identifiable mutations that can, if so desired, be used as germplasm to generate novel new plant cultivars. Additionally, the novel induced mutant alleles in different genomes of the polyploid, can be intercrossed to generate novel phenotypes having predetermined, desirable properties.

Thus, in one aspect, the present invention is directed to methods for producing mutants of a target gene in a polyploid plant by: constructing a polyploid plant having at least one functional copy of a target gene located exclusively in only one of the homoeologous or homologous genomes of said polyploid plant; contacting seeds derived from the constructed polyploid plant with an effective amount of at least one mutagenic agent; germinating the mutagenized seeds; and assaying seed (or other plant tissues and/or organs) from plants derived from the germinated, mutagenized seeds to identify mutants of the target gene. In another aspect, the present invention is directed to polyploid plants, containing a mutation in a target gene, produced by the foregoing methods. In yet another aspect, the present invention is directed to seeds derived from polyploid plants, containing a mutation in a target gene, produced by the foregoing methods.

As used herein:

The terms "polyploid", or "polyploidy" refer to organisms having more than the diploid (2n) number of chromosome sets, or genomes.

The terms "autopolyploid" or "autopolyploidy" refer to polyploid organisms in which the polyploidy arose by the duplication of one or more sets of chromosomes, or genomes.

The terms "allopolyploid", or "allopolyploidy" refer to polyploid organisms in which the polyploidy arose by genetically combining two or more complete sets of chromosomes (genomes) from genetically different parents.

The term "monoploid" refers to the minimum number of chromosomes that contain all of an organism's genetic information. The monoploid complement of chromosomes is represented by the letter "n".

The term "diploid" refers to twice the monoploid set of chromosomes, i.e., 2n chromosomes.

The term "tetraploid" refers to four times the monoploid set of chromosomes, i.e., 4n chromosomes.

The term "hexaploid" refers to six times the monoploid set of chromosomes, i.e., 6n chromosomes.

The term "genome" refers to all the genetic information possessed by one monoploid set of chromosomes, and an individual organism may be genetically constructed of several pairs of genomes.

The term "homologous genome" refers to the like duplicate genomes of an autopolyploid organism.

The term "homoeologous genome" refers to the similar genomes of an allopolyploid organism.

The term "genotype" refers to the genetic makeup of an organism.

The term "phenotype" refers to the physical trait or traits, associated with a particular gene. The term "phenotype" can also be used collectively to refer to the sum of all the traits that characterize an organism.

The terms "locus" or "genetic locus" refer to the physical location of a particular gene on a chromosome.

The term "isoform" refers to different forms of a protein encoded by related forms or alleles of a gene located at the same or at different loci as, for example, the different forms of the granule-bound starch synthase protein (GBSS) encoded by the gene located at the three waxy loci of hexaploid wheat. Or the different enzyme proteins encoded by the different mutant alleles of each of the waxy loci, in each of the genomes. Thus, the mutants described in EXAMPLES 1–3 herein all represent alterations of the waxy gene locus, hence they may control different isoforms of the GBSS enzyme protein, if any enzyme is actually produced.

The methods of the present invention utilize polyploid plants that have at least one pair of functional, target genes located exclusively in only one of their homoeologous, or homologous, genomes. Thus, for example, an allohexaploid species useful in the practice of the present invention will have null or recessive mutations in all copies of the target gene in two of its three pairs of homoeologous genomes. The remaining pair of target genes in the third homoeologous genome must be functional. Similarly, for example, an allotetraploid species useful in the practice of the present invention will have null or recessive mutations in one pair of the target genes in one of the two homoeologous genomes. The two copies of the target gene in the second homoeologous genome will be functional, and usually dominant.

Plants having null mutant gene pairs in one or more of the homoeologous genomes can be identified by means of techniques well known to those skilled in the art. For example, standard protein analytical techniques, such as sodium dodecylsulfate polyacrylamide gel electrophoresis (SDS-PAGE), can be used, by which proteins are separated on the basis of size. Or two-dimensional SDS-PAGE, by which proteins are first separated on the basis of charge, and then separated on the basis of size, may be utilized to identify the isoforms of a target protein encoded by the cognate genes located on each of the homoeologous genomes. Varieties of the plant species of interest can then be screened, using an appropriate analytical method, such as SDS-PAGE, to identify those varieties that lack specific isoforms, or which carry null mutants in one, or more, of the homoeologous genomes. Protein analytical techniques, including SDS-PAGE, useful in the practice of the present invention to identify polyploid plants that lack one or more isoforms of a target protein are discussed in Hames, B. D. and Rickwood, D., (eds) 1990. Gel Electrophoresis of Proteins-A Practical Approach. Oxford Univ. Press; Scopes, R. K. and Smith, J. A., 1997. Analysis of Proteins In Current Protocols in Molecular Biology. John Wiley & Sons.

The foregoing approach to identifying plants having null or recessive mutant genes in one or more of its pairs of homoeologous genomes, utilizing SDS-PAGE, has been used in allohexaploid wheat to identify the dominant, functional isoforms of the granule-bound starch synthase (GBSS) protein, encoded by the waxy locus associated with each of the three wheat genomes, designated A, B and D (Chao, et al. 1989, Theor. Appl. Genet. 78:495–504). Nakamura et al. (Japanese Journal of Breeding, 42:681–685, 1992) and Yamamori et al. (Euphytica 64:215–219, 1992) used SDS-PAGE to identify the three homoeologous GBSS isozymes, encoded by the three homoeologous genomes of hexaploid wheat, via analyses for the presence or absence of the GBSS enzyme in a large number of genetic lines and varieties (Accessions). Chao, et al. (Theor. Appl. Genet. 78:495–504) analysed genetic stocks in which a pair of chromosomes or part of a chromosome is missing, i.e., nullisomic stocks, or ditelosomic stocks using a cDNA probe of the wx locus of barley, for RFLP analyses of the chromosome loci. These analyses aided the research by Nakamura et al. (Japanese Journal of Breeding, 42:681–685, 1992) using SDS-PAGE to analyze over 1,800 wheat accessions from various parts of the world to identify genetic sources in which one or another of the homoeologous GBSS genes was inactive or deleted. Thus, Nakamura et al. (Japanese Journal of Breeding, 42:681–685, 1992) were able to identify, among Japanese wheats, wheat accessions carrying a null mutant at each of the A and B genome waxy loci. They also found spontaneous null waxy mutants in the D genome of two old land race accessions from China, Bai Huo, a semi-spring wheat, and Bai Huo Mai, a winter wheat, which then permitted them to develop fully wy wheats i.e., wheats which produced no GBSS, by recombination of the individual, homoeologous null loci to obtain genotypes with only null loci for the waxy trait. Nakamura et al. (Japanese Journal of Breeding, 42:681–685, 1992) also identified the varieties Kanto 79 and Kanto 107 as carrying null waxy mutations in both the A and B genomes, leaving the D genome with an active or dominant gene for the non-waxy trait.

In addition to analyzing the protein composition of polyploid plants in order to identify varieties carrying null genetic loci, it is also possible to clone the target genes located at each homoeologous locus and generate locus-specific nucleic acid probes that hybridize to mRNA transcribed from a specific homoeologous locus (Clark, et al, Plant Mol. Biol. 16:1099–1101, 1991). Thus, by routine DNA cloning and nucleic acid hybridization techniques, such as those set forth in Sambrook J., Fritsch, E. F., and Maniatis T., Molecular Cloning: A Laboratory Manual, 2nd Edition (1989), it is possible to screen polyploid plant varieties to identify those varieties that include null mutations of the target gene in one or more of the homoeologous chromosomes, i.e., varieties lacking a messenger RNA transcript derived from one or more of the homoeologous loci carrying the target genes.

The foregoing analytical methods, for identifying null mutations in one or more homoeologous loci of an allopolyploid plant, can also be applied to autopolyploid plant species, provided that the duplicated genomes have had sufficient time to diverge and accumulate sufficient mutations so that the gene products of either of the homologous loci bearing the target gene can be distinguished.

When varieties of a polyploid plant species have been identified that contain null mutations in the target gene(s) in one or more of the homoeologous, or homologous, genomes, it is then possible to selectively cross those mutant varieties in order to construct plants that contain other combinations of functional target genes in only one, specified homoeologous, or homologous, genome locus. By way of non-limiting example, other new combinations of null mutants of the waxy locus can be generated in hexaploid wheat, (1) by crossing the wheat variety AC Majestic (carrying the A genome nulls for waxy) with Bai Huo, one of the Chinese wheats which carry the D genome nulls for waxy. This cross will yield plants with A and D genome waxy null loci, but with the normal, dominant B genome non-waxy locus, thereby setting up the genotype for inducing waxy mutations in the B genome according to the practice of the present invention; (2) by crossing cv Klasic or ID377s, two wheats carrying the B genome waxy null loci, with Bai Huo, some F2 generation recombinants can be recovered which carry waxy null loci in both the B and D genomes, but with the dominant gene for the GBSS protein in the A-Wx locus. Seeds of these recombinants can be mutagenized according to the practice of the present invention to induce waxy null gene mutants in the A genome. Of course, in a polyploid plant such as wheat, for which diploid, tetraploid and hexaploid varieties exist, the task of introducing null mutations in a target gene into the genome of a hexaploid variety is greatly simplified if null mutants can be found among the tetraploid wheats, or if the screening system could identity a tetraploid or hexaploid wheat genotype which already has one or two of the homoeologous genomes, respectively, carrying a null mutation.

Once a polyploid plant line has been selected in which the functional copies of the target gene are located exclusively in only one homoeologous, or homologous, genome, then the subject plant/plant line can be mutagenized by contacting the plants with an effective amount of one or more mutagenic agents. Preferably, seeds from the subject plant line will be contacted with one or more mutagens. Numerous mutagenic agents are well known to those of ordinary skill in the art (IAEA Manual on Mutation Breeding-Tech. Reports Series 119, IAEA, Vienna, 1977). Radiation or beams of accelerated atomic particles can be used as mutagens. For example, gamma rays and fast neutron bombardment have been used to induce mutations in wheat. Preferably, however, chemical mutagens are utilized in the practice of the present invention, because of their ready availability and ease of application. Examples of chemical mutagens useful in the practice of the present invention include, but are not limited to, ethyl methanesulfonate (EMS); diethyl sulfate (DES) and sodium azide (AZ). Most preferably, the chemical mutagens used in the practice of the present invention are a sequential combination of EMS or DES, and sodium azide. The types of mutations that are induced by mutagenic agents useful in the practice of the present invention, include point mutations, deletions, inversions and substitutions of individual DNA base pairs, or of one or more DNA segments containing numerous DNA base pairs.

The preferred method for chemically mutating the single homoeologous, or homologous, genome bearing the sole functional pair of the target genes, includes sequential applications of chemical mutagens, such as ethyl methanesulfonate or diethyl sulfate, followed by a treatment with sodium azide (AZ). The treatments are preferably applied to seeds that have been presoaked for 4–6 hours at room temperature (20–23° C.) in either distilled water or tap water. The applications of the mutagens are preferably made in distilled water solutions, but tap water can be used provided that the tap water does not contain undue amounts of metals, especially, copper contaminants (IAEA Manual on Mutation Breeding-Tech. Reports Series 119, IAEA, Vienna, 1977). The EMS is applied at a concentration of 0.25–0.35 milliliters (ml) per liter distilled water for 2–2.5 hours. DES can be used at 1–2 ml per liter of distilled water for a treatment time of approximately 2 hours, prior to the AZ treatment. The EMS treatments are preferably followed by a treatment with $1\times10^{-3}$ to $2\times10^{-3}$ M AZ in $1\times10^{-3}$ M phosphate buffer (pH 3.0). No wash between treatments is necessary, but the EMS solution is poured off after the selected treatment time, and before the buffer is added prior to introducing the AZ from a concentrated stock solution. After the AZ treatment of 1–1.5 hour, the AZ solution is poured off, and the seeds are rinsed with distilled water before laying them out on screen trays for redrying. Redrying should preferably not exceed 24 hours before the seeds are planted to start germination, or are placed in a refrigerator at 2–6° C. When stored in a cool refrigerator, the treated seeds can be held for several months before planting, without an undue increase in mutagen-induced injury. There is less risk of delayed injury to seeds mutagenized with DES, because the reaction rate of DES is about 9× that of EMS with water (IAEA Manual on Mutation Ereeding-Tech. Reports Series 119, IAEA, Vienna, 1977).

Once the seeds have been treated with one or more mutagens, the seeds are germinated, the germinated plants (M1) are allowed to self-fertilize and M2 seed is harvested. The M2 seed can be assayed for the loss of activity of the target gene if, as is the case with the waxy trait, the mutation is a property characteristic of the seed. Additionally, any tissue, organ or material derived from any plant derived from the mutagenized seed can be assayed for the partial or complete loss of activity of the target gene.

The practice of the present invention thus requires that a target gene be identified in a particular tissue of the plant, and that an assay for a target gene product activity is available to identify those derivatives of mutagenized seed or plants that carry mutations of the target gene. One example of a suitable target gene is the gene located at the waxy locus, an endosperm trait, identified in several cereal crop species including wheat and oats. The protein encoded by the gene located at the way locus is involved in the biosynthesis of amylose starch from amylopectin starch, via debranching or linearizing the initially-synthesized amylopectin molecules, a process which is of considerable importance to the food industry. Starch from cereals, especially, consists mainly of two types of carbohydrate polymers; amylose, which is essentially linear, and amylopectin which is a highly branched carbohydrate polymer. In cereals, the starch granule-bound starch synthase enzyme (GBSS) controls the process of debranching the initially-formed amylopectin starch, leading to the formation of non-branched amylose starch. Both natural and induced mutations of the gene involved have been identified readily in many of the diploid species of cereals, and extensive research has shown that null or recessive mutants of the gene result in the production of almost 100% amylopectin starch, because the GBSS is non-functional, or the function is altered (Briggs, et al., Nature 207:891–892, 1965; Amano, E., Environ. Health Perspect. 37:35–41, 1981; Echt, C. S. and Schwarz, D., Genetics 99:275–284, 1981). A deviant, partially functional GBSS enzyme might less-effectively debranch the amylopectins, or have an unusual mode of action, resulting in the production of amylopectin starch molecules with different relative proportions of highly and less branched polymers.

In polyploid species, the biochemical genetics of the process of starch biosynthesis is somewhat more complicated than in the diploid species, such as rice, maize, and barley, but the general principles still hold. The amylose content of starch typically ranges from about 11–37% of total starch. The occurrence of a deletion or null mutation in fewer than all of the genomes of a polyploid species may reduce the amount of amylose synthesized, but enough amylose will still be formed by the remaining active GBSS gene to prevent detection of the change, except by methods for identifying the enzyme itself, rather than the product, or via a more exact analysis of the starch composition by a chemical method. A convenient, simple assay for waxy mutants that reduce, or completely abolish, the synthesis of amylose, is based on the observation that the adsorption of iodine by amylopectin and by amylose is greatly different. Thus, waxy mutants can be readily distinguished by applying an iodine solution, such as IKI (iodine+potassium iodide), to the cut surface of seed endosperm and observing the color of the product. Wax mutants are easily identified because non-mutant starch stains blue-black, while waxy starch stains red-brown.

There is considerable interest within the food industry in isolating null or recessive waxy mutant varieties of wheat, because the physical properties and functionality in foods or in industrial products and processes of flour are affected by the composition of the starch contained therein. For example, the "bite" or mouth feel, texture and palatability of white noodles are adversely affected by a high amylose content, and conversely, improved by an increase in the proportion of amylopectin starch, though it is not yet known if fully waxy wheats will make better noodles. Oda, M, Yasuda, Y., Okazaki, S., Yamaguchi, is and Yokoyama, Y. Cereal Chem. 57:253–254 (1980). Thus, it is desirable to isolate mutants in wheat, from which flour is derived for manufacturing noodles, that are lower in amylose in order to produce flour that yields a better quality noodle. Additionally, recent research has shown that the highly cross-linked type of starch, amylopectin, has a higher, longer water retention ability after cooking than starches containing more than 10% amylose. Because of this property, the baking industry has become interested in high amylopectin starch addition(s) to wheat flour to extend the shelf life of baked product since amylopectin starch may increase the water-holding capacity, and thus improve the staling properties of bread. Many other uses of a way (high amylopectin) wheat can be foreseen, including, but not limited to, applications for thickeners, baby foods and puddings, and glues which may not require as high amounts of emulsifiers and would likely have improved consumer reception. Further, the livestock industry is interested in obtaining wary varieties of cereals that are used as livestock feed because the greater branching structure of amylopectins makes the molecules more readily degradable by amylolytic enzymes, thus increasing the rate of energy availability to monogastric animals.

Other examples of suitable target genes include the genes that are involved in the biosynthesis of phytic acid. All seeds of both legumes and cereals contain phytic acid as the main storage form of phosphate in the seeds. Phytic acid is a myoinositol hexakisphosphate, which is important in seed germination and early development, but appears not to be essential to the plant, since inorganic phosphate can be accumulated to serve essentially the same function (Raboy, V., The Biochemistry and Genetics of Phytic Acid Synthesis. 1990. pp. 52–73. In: Inositol Metabolism in Plants. Morre, D. J., Boss W. F. and Loewus, F. A. (eds). Wiley-Liss, New York.). Phytic acid is also a very strong chelator of divalent mineral ions, such as Zn, Cu, Ca, Fe and Co, and is responsible for the excretion of the seed phosphates and minerals by animals, i.e., the phosphates and minerals are bound to the phytic acid and so are inaccessible for absorption by the gut. The animal excretions of phytic phosphate chelated minerals results in about 30% of the manure produced by poultry, and perhaps a similar amount produced by swine. These excess excrements not only contribute to environmental pollution, but also deny the animals of the mineral nutrients, which must be supplied from other sources. Null mutations of the genes controlling the enzymes responsible for phytic acid synthesis in seeds would prevent loss of the minerals from animal diets, reduce the amount of mineral pollutants released into the environment from manure and improve the utilization of minerals and phosphates from seeds fed to livestock.

Yet other examples of suitable target genes include genes encoding oxidases, lipases and lipoxygenases. In oats and peanuts, particularly, it is desirable to reduce or eliminate these enzymes, in order to reduce the oxidation or degradation of the seed oils for which oats, in particular, could become an important industrial source.

The greater concern over oxidase, lipase and lipoxygenase activities in oats is due to the fact that oat endosperm contains on average 5–6% oil, and the natural variation in the levels of oat seed oil suggests that the oil level could be increased to 16–18%, making oats a commercial oil source, if rancidity of the oil could be prevented by inactivating the degradative enzymes. In addition, oat oil contains a high proportion of tocopherol which is an important source of vitamin E. Tocopherol levels could also be enhanced by eliminating or reducing endogenous lipase and/or lipoxygenase activity.

A convenient and simple screening system for mutants having reduced or no lipoxygenase/lipase activity could be based on the ability of lipoxygenases/lipases to oxidize carotenoids (Hildebrand, D. E. et al. Current Topics in Plant Biochemistry and Physiology 7:201–219 (1988)). As with phytic acid, lipoxygenase and lipase are not essential to the growth of the plants, though these enzymes may function in insect or disease resistances (Hildebrand, et al, J. Econ. Entom. 79:1459–1465 (1986)). It may be possible to delete these enzymes from the seeds, without affecting their activity in the plants. These enzymes apparently affect the flavor of products made from soybeans. However, natural soybean mutants were found in the soybean germplasm, permitting the breeding of soybean cultivars lacking the peroxidases (Hildebrand, D. E. et al. Current Topics in Plant Biochemistry and Physiology 7:201–219 (1988)). In durum wheats, these enzymes cause the breakdown of carotenoids, which are highly important for pasta quality (Matsuo et al, Cereal Chem. 47:1(1970); Lee, et al., Theor. Appl. Genet. 47:243 (1976); McDonald, C. E., Cereal Chem. 56:84 (1979), Laignelet, B., Sci. Aliment. 3:469 (1983). Durums have been developed for increased carotenoid content of the flour or semolina from the endosperm, and over time cultivars have been developed with comparatively high levels of carotenoids. Such high levels of carotenoids have been achievable only by reducing the destruction of the pigment by lipoxygenases. Thus, these enzymes are not essential to the growth and vigor of the plants, but may still exist in crop species as relics from evolution for which they served to assure continued survival of the species by making the seed less palatable to wild animals. The chromosomal location of peroxidases in durum wheats is known, and tests for the activity of the enzymes are available (Kobrehel, K. and Fiellet, P., Can. J. Bot. 53:2336 (1975); Hseih, C. C. and McDonald, C. E., Cereal Chem. 61:392 (1984)). Achieving these high carotenoid levels, has been possible only by reducing or eliminating the activities of the oxidizing lipoxygenase enzymes (Lee, et al., Theor. Appl. Genet. 47:243 (1976); Kobrehel, K. and Gautier, M. F., Genetic Variability in Peroxidase Composition of Wheat. p. 527, In: Proc. Symp. on Genetics and Breeding of Durum Wheat. G. T. Scarascia-Muggnozza (ed.). Univ. de Bari. Bari. Italy, 1973). With durums, exposure of a sample of crude semolina to moist air for a period of hours is enough to cause loss of yellow pigment color, if peroxidase activity is present. Carotenoids are too oxygen-sensitive for use in a screening method, but some other luteins may prove useful as detectors of peroxidase activity in oats. Reports in the literature indicate that methyl-jasmonate may be useful to accelerate the reaction.

Another example of a suitable target gene isoform family includes polyphenol oxidases. Polyphenol oxidases occur almost universally in plants. These oxidases are responsible for the browning reaction of cut surfaces and bruises in apples and peaches. They are also the cause of browning or brown specks in pasta and soft wheat noodles made from wheats with high levels of polyphenol oxidase in their seed coats. The brown pigments and specks in noodles and pasta are repulsive to consumers. In the past, flours for noodles and pasta were produced at relatively low extraction, which largely avoided inclusion of bits of seed coat tissues in the flour or semolina. However, breeders of durum wheats have over the years developed durum cultivars that are either low in polyphenol oxidases or are completely free of the enzymes. Thus, durum breeders have discovered natural genetic variability for null alleles of the polyphenol oxidases in durums However, in hexaploid wheats, no genetic source of null polyphenol oxidase genes is available, though several wheat genetic stocks have been identified that have low polyphenol oxidase levels (Bernier, A. M. and Howes, N. K., J. Cereal Sci. 19:157–159 (1994)). Canadian scientists, have discovered a null locus for the enzyme in the diploid D-genome progenitor of hexaploid wheat, T. tazischii, hence have synthesized a genetic source of zero polyphenol oxidase in hexaploid wheat (Bemier and Howes, 1997, personal communication). However, because the wheat they developed is a synthetic, carrying many genes from the wild progenitor and the durum parent, the synthetic is not as useful as a source of the null alleles as would be a mutant induced in one of the modern hexaploid wheats with a low polyphenol oxidase activity. Thus, since a simple and rapid screening system has been developed (Bernier, A. M. and Howes, N. K., J. Cereal Sci. 19:157–159 (1994)), it will be readily feasible to apply the technology of this invention for the induction of hexaploid wheat mutants with reduced or zero polyphenol oxidase activity.

In addition to the foregoing examples of suitable target genes, it will be readily understood by one of ordinary skill in the art that the methods of the present invention are applicable to any gene for which a screening protocol is available with which to identify mutants in that gene. The methods of the present invention are applicable to any polyploid plant species including, but not limited to, the following agriculturally important, polyploid species:

Wheat-Triticum aestivum L. hexaploid cultivated common and club or compactum wheats, soft, hard, white, red, spring, and winter types.

Wheat-Triticum *turgidum durum*, tetraploid cultivated forms, which include durum (pasta wheats) and a special large kernel form, Triticum *turgidum turanicum.*

Oat-Avena sativa L., *Avena byzantina* L., and *Avena nuda* L. All hexaploid species, the latter is hulless oats.

Triticale-*Triticale hexaploide* Wittmack. Hexaploid triticale, a modem synthetic species constructed from T. turgidum (durum) x *Secale cereale* L. (rye). Cotton-*Gossypium hirsutum* L. now known to be a natural synthetic tetraploid constructed of *G. arboreum* L. x G. barbadense L.

Alfalfa-*Medicago sativa* L. is an allotetraploid (like cotton) constructed from M falcata L. x *M. glutinosa* L, which often shows tetrasomic inheritance of traits, indicative of genetic homeology Tobacco-*Nicotiana tabacum* L. an allotetraploid of natural origin, combining genomes from *N. sylvestris* Speg. x *N.*

*tomentosiformis* Goodsp. The genomes are similar enough to often show tetrasomic inheritance of some traits.

Peanut-*Arachis hypogea* L. is a probable allotetraploid for which the diploid progenitors are uncertain. However, the species carries traits, which indicate homeology between genomes (sets) of 10 chromosome pairs.

Coffee-*Caffea arabica* L. and *Caffea canephora* L are both tetraploid species, which like most others mentioned carry sets of chromosomes with much homeology Rapeseed and Mustards-*Brassica napus*. L ssp. *oleifera* (Metzg.) (Summer and winter rapeseed.), and *Brassica juncea* L. (brown, oriental mustard) are allotetraploids. Many grass species are polyploids, as are a number of other legumes, including Birdsfoot trefoil, *Lotus corniculatus* L.;

Sainfoin, *Onobrychus vicifolia Scop.*, Crownvetch, *Coronilla varia* L.;

Cicer rilkvetch, *Astragalzus cicer* L.; and Lupines, *Lupinus albus* L.,

*Lupinus angustifolius* L., and *Lupinus luteus* L., trefoils.

The practice of the present invention will be better understood with reference to the following examples.

EXAMPLE 1

Generation of Waxy Mutants of Wheat Line Kanto 107

The seeds (about 2.5 kg) of Kanto 107 wheat (carrying null waxy mutants in the A and B genomes) were presoaked (immersed in water) for 4–5 hr. prior to the mutagen treatments. The water used was tap water (although distilled water may be used.). After the presoaking period, the water was poured off, and a liter of distilled water was added to each container of seeds. The mutagen ethyl methane sulfonate (EMS) was applied to the seeds in the distilled water solution. The treatments applied included one treatment at 0.2 milliliter EMS per liter of distilled water, and two treatments at 0.25 milliliter of mutagen (EMS) per liter of distilled water. The seeds were allowed to soak in each of the mutagen solutions for 2 hours and 15 min., with shaking of the treatment containers every 15–20 min. during treatment to improve the contact of the seeds with the mutagen solutions. After this treatment, the EMS solutions were poured off into a container used for disposal, and one liter of $1 \times 10^{-3}$ molar phosphate buffer (pH=3) was added to each container. To each container with seeds and buffer, 1.5 milliliters of a 1.0 molar stock solution of sodium azide was added, and the containers were then shaken to distribute the mutagen. This azide treatment was continued with intermittent shaking (every 15 min.) for 1 hour, after which the solution was poured off into the disposal container, and the seeds in each container were given a distilled water rinse. After rinsing, the seeds were placed to redry in screen baskets in a fume hood. Redrying in the fume hood was continued for 14 hours, then the seeds were taken to another laboratory to continue redrying at room temperature for another 24 hours. At this point, the treated seeds were placed in seeder magazines and planted in the field, much as any seeds would be sown for production.

Weed control during the growing season involved the use of the standard herbicides, Bronate and Hoelon. At maturity, the crop of each was harvested with an experimental combine (Wintersteiger Seedmaster). Production was about 420 kg after harvest, the seeds of each lot were stored for 1–3 months, after which the seeds were cleaned of debris and readied for mutant analysis. Candidate recessive waxy (wx) mutants of Kanto 107 were selected from among others in the bulk M2 seed lots by their visual appearance (waxy seeds have an opaque, lighter, near yellowish-white coloration). The posterior portion of the endosperms from the candidate mutant seeds were excised and the embryo end of each was tested with an iodine-potassium iodide solution, (stock solution=3 gr Iodine ($I_2$) crystals: 15 gr potassium Iodide (KI) crystals/100 ml distilled water; this solution, kept in a brown bottle, away from light, was diluted 1:10 with distilled water for the seed tests. Non-waxy seeds stained a dark blue color, while waxy (wx) seeds stained a reddish-brown color. Seeds with a yellow-berry condition (an environmentally influenced trait) are often confused with wx seeds, but the stain test is definitive. An initial screen yielded 45 mutants from only 25 lbs. of M2 seed from mutagenized Kanto 107, and more M2 seeds are still available for selecting additional mutants.

EXAMPLE 2

Generation of Waxy Wheat Mutants of Hard Red, Winter Wheat cv. Ike

A recently-released Kansas hard red winter wheat, cv. Ike, also was mutagenized. Like Kanto 107, Ike carries natural, or spontaneous null waxy mutations in its A and B genomes. A similar set of mutagen treatments was applied to seeds of Ike as was applied to Kanto 107 seeds (as set forth in EXAMPLE 1), except that the two mutagen treatments applied were 0.25 ml EMS per liter of distilled water and 0.3 ml EMS per liter of distilled water, followed by the same azide treatment. After the mutagen treatments were applied to the Ike seeds, the seeds were redried, then placed into paper towel "boats", wetted and dosed with Captan fungicide, and allowed to start growth in the greenhouse for 3 days. After their growth was started, the containers of treated seeds were placed in a cold room at 4–6° C. for 7 weeks to vernalize them (satisfy their winter growth trait). Following vernalization treatment, the seedlings which germinated during the cold treatment were transplanted to greenhouse benches and grown to maturity. At maturity, the plants were harvested, the seeds threshed, cleaned and screened for wx (waxy) mutants following the same procedure as described in EXAMPLE 1 for M2 seeds from the mutagenized Kanto 107. From the M2 generation of mutagenized seeds (seeds produced by the M1 plants), nine waxy mutants were selected. All were confirmed via tests of the M3 generation seeds grown on plants from the selected M2 waxy seeds.

EXAMPLE 3

Characterization of Wary Kanto 107 Mutants

Several Kanto 107 waxy mutants (created and identified as set forth in EXAMPLE 1) were analyzed with respect to various physical and biological parameters. Control, non-waxy varieties were included in the analyses for comparisons, and a wady line, carrying the natural or spontaneous mutant D-genome null allele from Bai Huo, was included as well. In the subsequent discussion of the data set forth in Tables 1 and 2, and FIGS. 1–3, seed sample 0 is the original Kanto 107 variety which carries two waxy null gene loci; seed samples 1 and 4–25 are waxy mutants derived from mutagenized Kanto 107 seed; seed sample 3 is a partially-penetrant way mutant, i.e., a mutant which does not show the full waxy phenotype; seed sample 26 is a soft white, spring wheat, cv. Penawawa, which carries a single waxy null gene at the B locus, and seed sample 27 is a soft white, spring wheat, cv. Alpowa, which does not carry any waxy null gene loci. Sample 30 contains a naturally-occurring waxy null mutant in each of the three homoeologous wheat genomes, A, B and D.

Table 1 sets forth the characteristics of the prime starch extracted from flour milled from the foregoing wheat seed samples. The starch fractions were separated from the flour, via a process developed by Czuchajowska, Z. and Pomeranz, Y., Cereal Chem. 70(6):701–706, and as disclosed in U.S. Pat. No. 5,439,526. Prime starch is the essentially pure starch fraction, containing only unbroken starch granules, and separated from the principal protein fractions in the flour; it has a very low ash content and is very low in protein. The prime starch still contains small amounts of phospholipids and a very minor fraction of proteins mostly associated with the starch granules. In Table 1, data are presented comparing the amylograph analyses of the prime starch fractions of the various wheats. The amylographic data were generated by standard techniques set forth in Shuey W. C. and Tripples, K. H., (eds.) The Amylograph Handbook, 1980, Am. Assoc. Cereal Chem., St. Paul, Minn., which is incorporated herein by reference. The data include the temperature at which the peak (highest) viscosity occurs, the actual recorded viscosity of the solubilized starch at the peak temperature, the viscosity 5 minutes after the peak viscosity was reached, the viscosity at the end of a period of 30 minutes holding at the peak temperature, and at the end of a period of 30 minutes holding the gelled starch at 50° C.

TABLE 1

Prime Starch-Amylograph

| Seed Sample | Name | Temp. C. of Peak | Peak Viscosity | 5 min. after Peak | End of holding at Peak | End of holding at 50° C. |
|---|---|---|---|---|---|---|
| 0 | Kanto 107 (control) | 93.50 | 1040 | 860 | 620 | 1040 |
| 1 | K107 wx 1 | 70.00 | 1540 | 1000 | 680 | 650 |
| 3 | K107 partial wx | 95.00 | 930 | 740 | 520 | 490 |
| 4 | K107 wx 4 | 71.00 | 1540 | 1160 | 860 | 830 |
| 9 | K107 wx 9 | 68.50 | 1580 | 1040 | 670 | 720 |
| 10 | K107 wx 10 | 69.00 | 1500 | 1000 | 640 | 690 |
| 12 | K107 wx 12 | 68.00 | 1490 | 1000 | 660 | 680 |
| 13 | K107 wx 13 | 68.00 | 1480 | 960 | 610 | 620 |
| 14 | K107 wx 14 | 68.00 | 1500 | 1000 | 640 | 670 |
| 15 | K107 wx 15 | 67.50 | 1500 | 1000 | 660 | 670 |
| 16 | K107 wx 16 | 68.00 | 1430 | 900 | 610 | 650 |
| 18 | K107 wx 18 | 68.00 | 1800 | 1610 | 720 | 720 |
| 21 | K107 wx 21 | 67.00 | 1880 | 1200 | 740 | 730 |
| 22 | K107 partial wx | 72.00 | 1620 | 1450 | 1300 | 1210 |
| 25 | K107 wx 25 | 68.00 | 1500 | 1010 | 650 | 670 |
| 26 | Penawawa (1 wx) | 95.00 | 680 | 980 | 620 | 610 |
| 27 | Alpowa (0 wx) | 96.00 | 360 | 390 | 450 | 1040 |
| 30 | HWSW96004 (nat. wx) | 67.00 | 1800 | 1170 | 780 | 820 |

The data clearly demonstrate differences among the mutants and the standards. Kanto 107 mutant 3 appears to be a partially waxy line, but it was first identified as waxy, like all the rest, but the seed harvested from the M2 and M3 plants proved not to stain red like typical waxy mutants, thus was thought to have been selected in error, but seed of it was increased anyway in order to have a single line selection from Kanto 107. However, as the Amylograph data show, mutant 3 has many properties similar or intermediate between those of Kanto 107 (0), and the truly waxy mutants 1, 4–25. Mutant 3 must contain a fair amount of amylose, since its peak gelatinization temperature is much like that of Penawawa, though its peak viscosity is more nearly like that of Kanto 107. Its amylopectin content is presumably intermediate between that of Kanto 107 and a more fully waxy mutant, having nearly 99% amylopectin. Of special interest are the peak viscosity data for mutants 9 and 21. The gels of these mutants have a rather high viscosity at their peak temperature of gelling.

In table 2, the texture of gels made from the prime starch of the mutants and controls was measured after storing the gels at 4° C. for 96 hr. after gelling.

TABLE 2

Prime Starch-Gel Texture

| | | Time of Storage (hours) | | |
|---|---|---|---|---|
| Seed Sample | Name | 0 | 48 | 96 |
| 0 | Kanto 107 (control) | 1.983 | 3.575 | 3.618 |
| 1 | K107 wx 1 | 0.669 | 0.694 | 0.880 |
| 3 | K107 partial wx | 2.058 | 2.879 | 2.883 |
| 4 | K107 wx 4 | 0.423 | 0.510 | 0.533 |
| 9 | K107 wx 9 | 0.456 | 0.571 | 0.577 |
| 10 | K107 wx 10 | 0.418 | 0.498 | 0.526 |
| 12 | K107 wx 12 | 0.371 | 0.455 | 0.457 |
| 13 | K107 wx 13 | 0.251 | 0.374 | 0.399 |
| 14 | K107 wx 14 | 0.371 | 0.481 | 0.452 |
| 15 | K107 wx 15 | 0.342 | 0.429 | 0.390 |
| 16 | K107 wx 16 | 0.262 | 0.398 | 0.381 |
| 18 | K107 wx 18 | 0.447 | 0.550 | 0.519 |
| 21 | K107 wx 21 | 0.480 | 0.542 | 0.515 |
| 22 | K107 partial wx | 0.588 | 0.726 | 0.681 |
| 25 | K107 wx 25 | 0.322 | 0.430 | 0.472 |
| 26 | Penawawa (1 wx) | 5.713 | 6.515 | 7.104 |
| 27 | Alpowa (0 wx) | 6.902 | 8.295 | 8.107 |
| 30 | HWSW96004 (nat. wx) | 0.241 | 0.268 | 0.330 |

Gel texture was measured according to the methods set forth in Czuchajowski, Z. T. et al., Composition, Thermal Behavior, and Gel structure of Prime and Tailing Starches from Garbanzo Beans and Peas, 1998 Cereal Chem. 75. The texture of the gels from starches of different mutants differed markedly from those of the controls, which generally formed stiffer gels, which increased significantly in stiffness, as measured in Newtons (N), as the gels were stored. All of the mutants analysed, except for mutant 3, had markedly softer gels, though each mutant seemed to differ slightly from the others. The changes in texture over time for most mutants was generally less than that of controls. Mutants 13 and 16 had very low viscosity levels, with modest increases over time. In contrast, mutants 9 and 21 started at modest levels, and changed very little over time. Some other mutants followed a similar pattern, but began at either lower or higher texture levels. The stability over time and temperature of gels made from starches is an extremely important factor in the selection of materials for food products. Interestingly, mutant 3 shows an unusual gel texture under the test conditions. Although the gel made from its prime starch had an initial texture slightly higher than that of Kanto 107, the gel texture increase much less over time of storage. Clearly, the starches from these mutants are not all alike, thus they offer the potential for developing unique wheat starch sources for special industrtial or food products.

Figure 2:
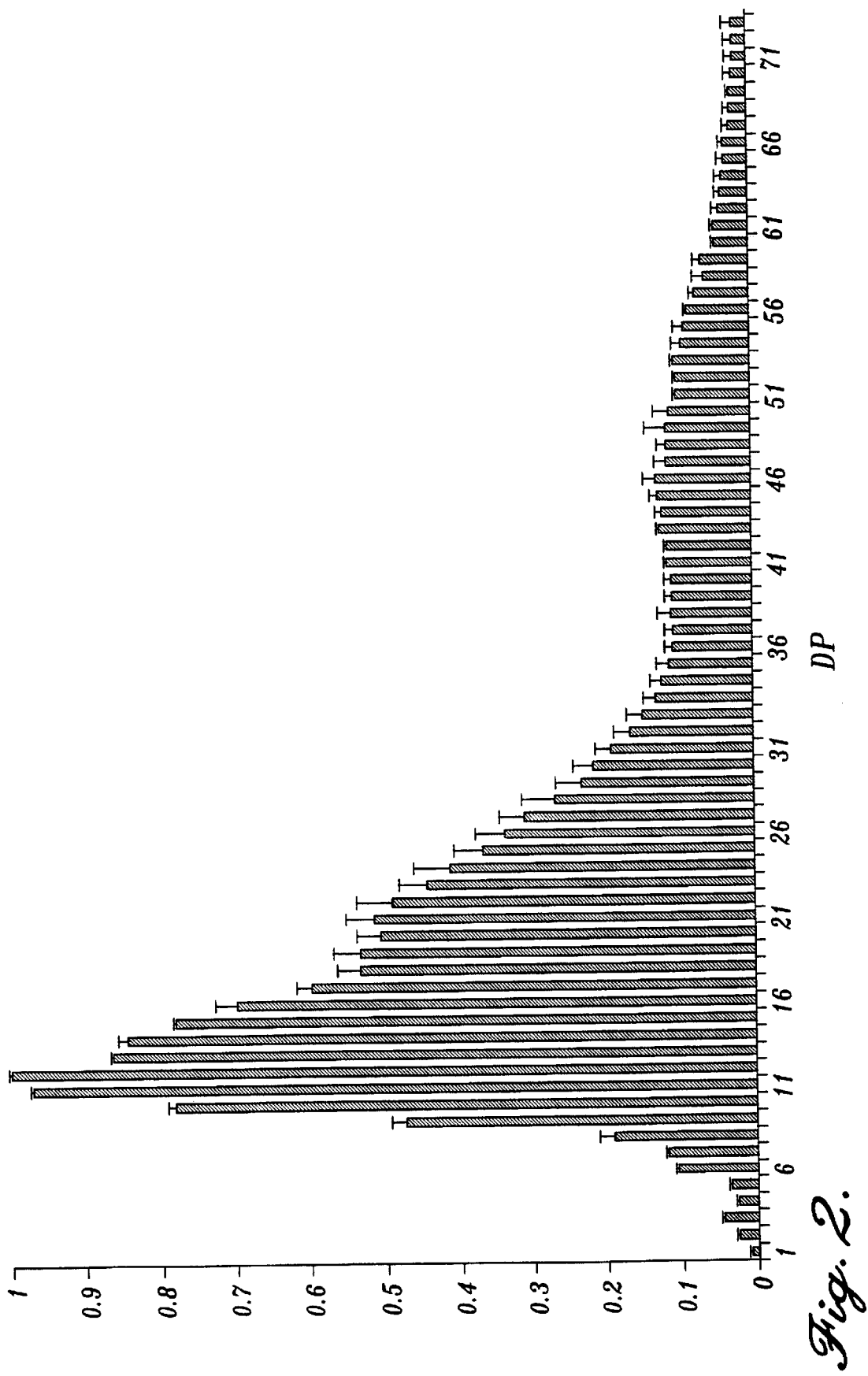
FIG. 2 graphically illustrates the degree of polymerization of starch molecules derived from waxy wheat mutant 22 derived from Kanto 107 as set forth in EXAMPLES 1 and 3. The x-axis represents the normalized peak area that is indicative of the amount of starch molecules having a degree of polymerization that is indicated by the y-axis.
Figure 3:
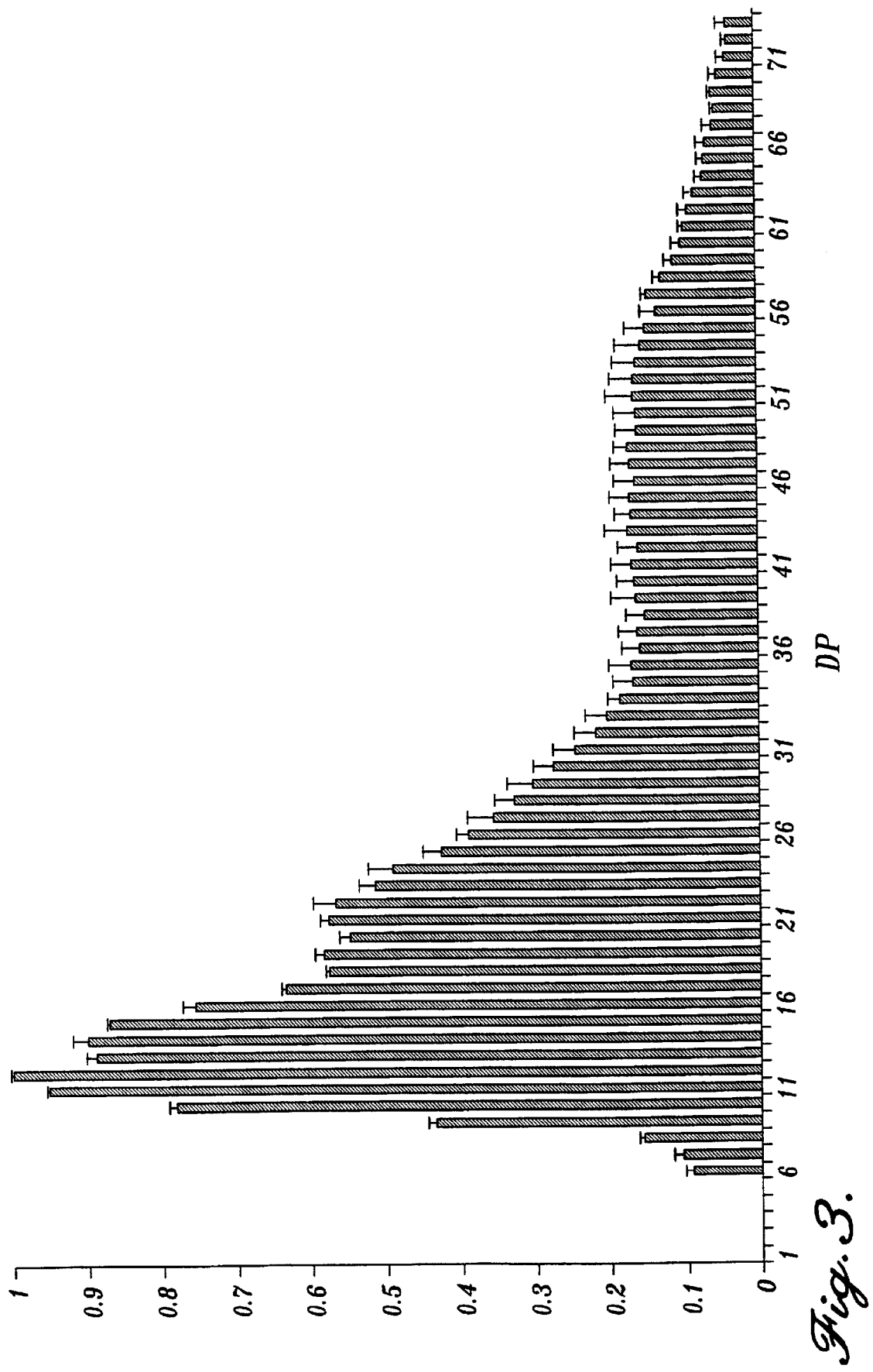
FIG. 3 graphically illustrates the degree of polymerization of starch molecules derived from waxy wheat mutant 4 derived from Kanto 107 as set forth in EXAMPLES 1 and 3. The x-axis represents the normalized peak area that is indicative of the amount of starch molecules having a degree of polymerization that is indicated by the y-axis.

Several of the mutants also appear to have distinctly different polymer compositions based on analyses by High Performance Size Exclusion Chromatograpy, after alpha amylase debranching of the starch polymers. As will be seen from FIGS. 1–3, the sizes of the polymers in the starches from some of the mutants listed in Tables 1 and 2, in relation to their degree of polymerization, differ notably. FIG. 1 shows that mutant 21 has a greater proportion of higher molecular weight polymers than does mutant 18. As shown in FIGS. 2 and 3, mutant 22 has more low molecular weight starch polymers, while mutant 4 has a distinctly higher proportion of higher molecular weight polymers in its make-up. These differences show that different mutant alleles have been induced, since all mutants described are expected to be at the same D-genome waxy locus. Moreover, electrophoretic analyses of the waxy Kanto 107 mutants show that some of the mutants, of those so far analysed, have an apparently non- or less- functional D-genome GBSS protein, while some others, though they produce a different spectrum of high molecular weight amylopectin polymers, appear to be null locus mutants. Thus mutants 5, 7, 8, 11, 12, 14, 15, and 18 appear to have no protein at the position typical for the D-GBSS protein band, Mutants 1, 9, 13, 16, and 17 appear to have a fairly strong D-genome way protein band. Mutants 4, 6, and 10 have a faint protein band at the D-genome Wx protein band position. More detailed analyses may yet show that some of the apparently null mutants carry proteins, which move to a different position in the electrophoresis gels. Nevertheless, it is quite clear that the different mutants result from a variety of alteration in the gene locus controlling the production of the D-genome GBSS protein. Those mutants with D-genome protein bands clearly must carry modifications in the GBSS enzyme which make them differentially functional or non-functional in their debranching capability. Similarly those mutants with a faint level of the protein must also be able to produce enough of a non- or nearly- non-functional enzyme to show up in the electrophoresis gels.

The above observations demonstrate that individual wax mutants may differ in the polymer composition of their waxy starch. It is desirable to generate as many waxy mutants as possible in order to identify those mutants having starch with desirable properties, such as increased functionality for use in various foodstuffs and as starting material for chemical modifications.

While the preferred embodiment of the invention has been illustrated and described, it will be appreciated that various changes can be made therein without departing from the spirit and scope of the invention.

What is claimed is:

1. A method for producing mutants of a target gene in a wheat plant, comprising;
   constructing a wheat plant having at least one functional copy of a target gene located exclusively in only one of the homoeologous or homologous genomes of said wheat plant;
   consecutively contacting seeds derived from the constructed wheat plant with an effective amount of at least two mutagenic agents to yield mutagenized seeds;
   germinating said mutagenized seeds; and
   assaying seed from wheat plants derived from said germinated, mutagenized seeds to identify mutants of the target gene.

2. The method of claim 1 wherein the seeds derived from the constructed wheat plant are contacted with a chemical mutagenic agent.

3. The method of claim 2 wherein the chemical mutagenic agent is selected from the group consisting of ethyl methanesulfonate, diethyl sulfate and sodium azide.

4. The method of claim 1 wherein the seeds derived from the constructed wheat plant are contacted with a first chemical mutagenic agent selected from the group consisting of ethyl methanesulfonate and diethyl sulfate, and are then contacted with sodium azide.

5. The method of claim 4 wherein the seeds are soaked in water for from about four to about six hours before being contacted with a chemical mutagenic agent.

6. The method of claim 4 wherein ethyl methanesulfonate is utilized at a concentration of from about 0.25 milliliters to about 0.35 milliliters per liter of water.

7. The method of claim 6 wherein the seeds are contacted with ethyl methanesulfonate for a period of from about two hours to about two and a half hours.

8. The method of claim 4 wherein diethyl sulfate is utilized at a concentration of from about 1.0 milliliters to about 2.0 milliliters per liter of water.

9. The method of claim 8 wherein the seeds are contacted with diethyl sulfate for a period of from about two hours to about two and a half hours.

10. The method of claim 4 wherein sodium azide is utilized at a concentration of from about $1 \times 10^{-3}$M to about $2`10^{-3}$M.

11. The method of claim 10 wherein the seeds are contacted with sodium azide for a period of from about one hour to about one and a half hours.

12. The method of claim 1 wherein the mutagenized seeds are germinated within about two hours after being contacted with an effective amount of at least two mutagenic agents.

13. The method of claim 1 wherein said target gene is involved in starch biosynthesis.

14. The method of claim 1 wherein said target gene is involved in phytic acid biochemistry.

15. The method of claim 1 wherein said target gene encodes a lipase.

16. The method of claim 1 wherein said target gene encodes a lipoxygenase.

17. The method of claim 1 wherein said target gene encodes a polyphenol oxygenase.

18. A method for producing mutants of a target gene in a wheat plant, comprising;
    constructing a wheat plant having at least one functional copy of a target gene located exclusively in only one of the homoeologous or homologous genomes of said wheat plant;
    consecutively contacting seeds derived from the constructed wheat plant with an effective amount of at least two mutagenic agents to yield mutagenized seeds;
    germinating said mutagenized seeds; and
    assaying wheat plants derived from said germinated, mutagenized seeds to identify mutants of the target gene.

* * * * *

UNITED STATES PATENT AND TRADEMARK OFFICE
CERTIFICATE OF CORRECTION

PATENT NO. : 6,696,294 B1  Page 1 of 7
APPLICATION NO. : 09/719880
DATED : February 24, 2004
INVENTOR(S) : C.F. Konzak It is certified that error appears in the above-identified patent and that said Letters Patent is hereby corrected as shown below:

| COLUMN | LINE | ERROR |
|---|---|---|
| Title Page Item (56) | Refs. Cited (Other Publs., Item 21) | "IAE-A-PL-412-15," should --IAEA-PL-412-15,-- |
| Title Page Item (57) | Reference Little R. Abstract LN 6 | "Seed derived" should read --Seeds derived-- |
| (57) | Abstract LN 8 | "seed are" should read --seeds are-- |
| (57) | Abstract LN 9 | "therefrom, are" should read --therefrom are-- |
| 1 | 35 | "Polyploid, is" should read --Polyploid is-- |
| 1 | 66 | "genome, are" should read --genome are-- |
| 2 | 1 | "of two," should read --of two-- |
| 2 | 6 | "DNA, termed" should read --DNA termed-- |
| 2 | 8 | "varieties, results" should read --varieties results-- |
| 2 | 34 | "invention, represents" should read --invention represents" |
| 2 | 39 | "grain cereals" should read --grain cereals,-- |
| 2 | 46 | "methanesulfonate" should read --methane sulfonate-- |
| 2 | 54 | "1982)" should read --1982),-- |
| 3 | 54 | "resistance, of" should read --resistance of-- |
| 3 | 30 | "mutations, has" should read --mutations has-- |
| 3 | 39 | " 'mutants' " should read --"mutants"-- |

UNITED STATES PATENT AND TRADEMARK OFFICE
CERTIFICATE OF CORRECTION

PATENT NO. : 6,696,294 B1
APPLICATION NO. : 09/719880
DATED : February 24, 2004
INVENTOR(S) : C.F. Konzak It is certified that error appears in the above-identified patent and that said Letters Patent is hereby corrected as shown below:

| COLUMN | LINE | ERROR |
|---|---|---|
| 3 | 43 | "event, for" should read --event for-- |
| 3 | 46 | "new mutants," should read --new mutants-- |
| 3 | 48 | "convey for" should read --convey, for-- |
| 3 | 51 | "new, or modified" should read --new or modified-- |
| 3 | 51 | "quality characteristics," should read --quality characteristics-- |
| 4 | 12 | "Seed derived" should read --Seeds derived-- |
| 4 | 14 | "agent, the" should read --agent; the-- |
| 4 | 14 | "seed are" should read --seed is-- |
| 4 | 15 | "therefrom, are" should read --therefrom are-- |
| 4 | 23 | "Seed derived" should read --Seeds derived-- |
| 4 | 25 | "agent, the" should read --agent; the-- |
| 4 | 25 | "seed are" should read --seed is-- |
| 4 | 26 | "therefrom, are" should read --therefrom are-- |
| 4 | 43 | "polyploid, can" should read --polyploid can-- |
| 4 | 54 | "way wheat" should read --*waxy* wheat-- |
| 5 | 14 | "polyploid, can" should read --polyploid can-- |
| 5 | 19 | "by:" should read --by-- |
| 5 | 29 | "plant, containing" should read --plants containing-- |
| 5 | 29 | "gene, produced" should read --gene produced-- |
| 5 | 31 | "polyploid plants," should read --polyploid plants-- |

UNITED STATES PATENT AND TRADEMARK OFFICE
CERTIFICATE OF CORRECTION

PATENT NO.         : 6,696,294 B1
APPLICATION NO. : 09/719880
DATED              : February 24, 2004
INVENTOR(S)        : C.F. Konzak It is certified that error appears in the above-identified patent and that said Letters Patent is hereby corrected as shown below:

| COLUMN | LINE | ERROR |
|---|---|---|
| 5 | 32 | "target gene," should read --target gene-- |
| 5 | 36 | " "polyploid", " should read --"polyploid"-- |
| 5 | 43 | " "allopolyploid", " should read --"allopolyploid"-- |
| 6 | 1 | "traits," should read --traits-- |
| 6 | 12 | "Or the different" should read --Or "isoform" may refer to the different-- |
| 6 | 16 | "locus," should read --locus;-- |
| 6 | 45 | "screened," should read --screened-- |
| 6 | 54 | "Proteins In" should read --Proteins. In-- |
| 6 | 61 | "protein, encoded" should read --protein encoded-- |
| 6 | 67 | "isozymes," should read --isozymes-- |
| 7 | 20 | "wy" should read --*waxy*-- |
| 7 | 20 | "wheats i.e.," should read --wheats; i.e.,-- |
| 7 | 34 | "et al," should read --et al.,-- |
| 7 | 45 | "methods, for" should read --methods for-- |
| 7 | 47 | "plant, can" should read --plant can-- |
| 8 | 31 | "invention, because" should read --invention because-- |
| 8 | 34 | "methanesulfonate" should read --methane sulfonate-- |
| 8 | 40 | "invention, include" should read --invention include-- |

UNITED STATES PATENT AND TRADEMARK OFFICE
CERTIFICATE OF CORRECTION

PATENT NO. : 6,696,294 B1
APPLICATION NO. : 09/719880
DATED : February 24, 2004
INVENTOR(S) : C.F. Konzak It is certified that error appears in the above-identified patent and that said Letters Patent is hereby corrected as shown below:

| COLUMN | LINE | ERROR |
|---|---|---|
| 8 | 46 | "genes, includes" should read --genes includes-- |
| 8 | 47-48 | "methane-sulfonate" should read --methane sulfonate-- |
| 8 | 55 | "especially," should read --especially-- |
| 8 | 65 | "time, and" should read --time and-- |
| 8 | 67 | "1-1.5 hour," should read --1-1.5 hours,-- |
| 9 | 8 | "DES," should read --DES-- |
| 9 | 10 | "Ereeding-Tech." should read --Breeding-Tech.-- |
| 9 | 29 | "way" should read --*waxy*-- |
| 9 | 49 | "less-effectively" should read --less effectively-- |
| 10 | 6 | "Wax" should read --*waxy*-- |
| 10 | 18 | "Oda, M," should read --Oda, M.,-- |
| 10 | 19 | "Yamaguchi, is" should read --Yamaguchi, S.-- |
| 10 | 26 | "than starches" should read --than have starches-- |
| 10 | 30 | "baked product" should read --baked products-- |
| 10 | 32 | "way" should read --*waxy*-- |
| 10 | 37 | "wary" should read --*waxy*-- |
| 10 | 47 | "hexakisphosphate, which" should read --hexakisphosphate which-- |
| 10 | 53 | "Boss, W.F." should read --Boss, W.F.-- |
| 10 | 57 | "animals, i.e.," should read --animals; i.e.,-- |

UNITED STATES PATENT AND TRADEMARK OFFICE
CERTIFICATE OF CORRECTION

PATENT NO. : 6,696,294 B1
APPLICATION NO. : 09/719880
DATED : February 24, 2004
INVENTOR(S) : C.F. Konzak It is certified that error appears in the above-identified patent and that said Letters Patent is hereby corrected as shown below:

| COLUMN | LINE | ERROR |
|---|---|---|
| 11 | 9-10 | Do not begin a new paragraph with the sentence "The greater concern over oxidase, lipase and lipoxygenase activities in oats...." |
| 11 | 28 | "et al," should read --et al.,-- |
| 11 | 30 | "seeds, without" should read --seeds without-- |
| 11 | 38 | " et al," should read --et al.,-- |
| 11 | 56 | "levels, has" should read --levels has-- |
| 12 | 20 | "durums However," should read --durums. However,-- |
| 12 | 24 | "scientists, have" should read --scientists have-- |
| 12 | 26 | "T. tazischii," should read --*T. tauschii*,-- |
| 12 | 48 | "aestivum" should read --*aestivum*-- |
| 12 | 54 | "Triticum" should read --*Triticum*-- |
| 12 | 55 | "Oat-Avena sativa" should read --Oat-*Avena sativa*-- |
| 12 | 56 | "species," should read --species;-- |
| 12 | 59 | "turgidum" should read --*turgidum*-- |
| 12 | 59 | "Cotton-" should begin a new paragraph |
| 12 | 60 | "L. now" should read --L, now-- |
| 12 | 61 | "G. barbadense" should read --*G. barbadense*-- |
| 12 | 63 | "falcata" should read --*falcata*-- |
| 12 | 63 | "L," should read --L-,-- |
| 12 | 65 | "homeology" should read --homeology.-- |

UNITED STATES PATENT AND TRADEMARK OFFICE
CERTIFICATE OF CORRECTION

PATENT NO.        : 6,696,294 B1
APPLICATION NO. : 09/719880
DATED             : February 24, 2004
INVENTOR(S)       : C.F. Konzak It is certified that error appears in the above-identified patent and that said Letters Patent is hereby corrected as shown below:

| COLUMN | LINE | ERROR |
|---|---|---|
| 12 | 66 | "L." should read --L.,-- |
| 13 | 5 | "traits, which" should read --traits which-- |
| 13 | 7 | "Caffea canephora" should read --*Caffea canephora*-- |
| 13 | 9 | "homeology" should read --homeology.-- |
| 13 | 10 | "oleifera" should read --*oleifera*-- |
| 13 | 11 | "rapeseed.)," should read --rapeseed),-- |
| 13 | 31 | "used.)." should read --used).-- |
| 13 | 54 | "14 hours," should read --14 hours;-- |
| 14 | 22 | "natural," should read --natural-- |
| 14 | 50 | "Wary Kanto" should read --*Waxy* Kanto-- |
| 14 | 55 | "wady" should read --*waxy*-- |
| 14 | 62 | "way mutant," should read --*waxy* mutant,-- |
| 15 | 5 | "flour," should read --flour-- |
| 15 | 18 | "Shuey" should read --Shuey,-- |
| 16 | 7 | "table 2," should read --Table 2,-- |
| 16 | 57 | "increase" should read --increased-- |
| 16 | 58 | "alike," should read --alike;-- |
| 16 | 60 | "industrtial" should read --industrial-- |
| 17 | 14 | "Thus" should read --Thus,-- |
| 17 | 16 | "band, Mutants" should read --band. Mutants-- |

UNITED STATES PATENT AND TRADEMARK OFFICE
CERTIFICATE OF CORRECTION

PATENT NO. : 6,696,294 B1
APPLICATION NO. : 09/719880
DATED : February 24, 2004
INVENTOR(S) : C.F. Konzak It is certified that error appears in the above-identified patent and that said Letters Patent is hereby corrected as shown below:

| COLUMN | LINE | ERROR |
| --- | --- | --- |
| 17 | 17 | "way" should read --*waxy*-- |
| 17 | 28 | "Similarly" should read --Similarly,-- |
| 17 | 32 | "wax" should read --*waxy*-- |
| 17 (Claim 1, | 45 line 2) | "comprising;" should read --comprising:-- |
| 18 (Claim 10, | 27 line 3) | "2'10$^{-3}$M." should read --2x10$^{-3}$M.-- |
| 18 (Claim 18, | 46 line 2) | "comprising;" should read --comprising:-- |

Signed and Sealed this

Eighth Day of August, 2006

JON W. DUDAS
*Director of the United States Patent and Trademark Office*